united States Patent
McMichael

(10) Patent No.: US 7,629,312 B2
(45) Date of Patent: Dec. 8, 2009

(54) METHOD OF TREATMENT OF TENDONITIS BY ADMINISTRATION OF STREPTOLYSIN O

(75) Inventor: John McMichael, Delanson, NY (US)

(73) Assignee: Milkhaus Laboratory, Inc., Delanson, NY (US)

( * ) Notice: Subject to any disclaimer, the term of this patent is extended or adjusted under 35 U.S.C. 154(b) by 349 days.

(21) Appl. No.: 11/688,596

(22) Filed: Mar. 20, 2007

(65) Prior Publication Data

US 2007/0219119 A1 Sep. 20, 2007

Related U.S. Application Data

(63) Continuation-in-part of application No. 10/764,161, filed on Jan. 23, 2004, now Pat. No. 7,196,058, which is a continuation-in-part of application No. 10/349,606, filed on Jan. 23, 2003, now Pat. No. 6,998,121.

(51) Int. Cl.
A01N 37/18 (2006.01)
A01N 43/04 (2006.01)
A61K 39/00 (2006.01)

(52) U.S. Cl. .......................... 514/2; 514/23; 424/198.1

(58) Field of Classification Search ........................ None
See application file for complete search history.

(56) References Cited

U.S. PATENT DOCUMENTS

| 5,240,846 | A | 8/1993 | Collins et al. |
| 5,292,498 | A | 3/1994 | Boucher, Jr. |
| 5,420,116 | A | 5/1995 | Puchelle et al. |
| 5,470,838 | A | 11/1995 | von Borstel et al. |
| 5,576,289 | A | 11/1996 | McMichael |
| 5,726,160 | A | 3/1998 | McMichael |
| 5,736,508 | A | 4/1998 | McMichael |
| 5,948,768 | A | 9/1999 | McMichael et al. |
| 5,955,442 | A | 9/1999 | McMichael |
| 6,096,721 | A | 8/2000 | McMichael |
| 6,303,127 | B1 | 10/2001 | McMichael et al. |
| 6,447,820 | B1 | 9/2002 | Niazi |

FOREIGN PATENT DOCUMENTS

| WO | WO-9211016 | 7/1992 |
| WO | WO-9312240 | 6/1993 |
| WO | WO-9423048 | 10/1994 |
| WO | WO-9525800 | 9/1995 |
| WO | WO-9632138 | 10/1996 |
| WO | WO-9640059 | 12/1996 |
| WO | WO-9705195 | 2/1997 |

OTHER PUBLICATIONS

Alton, E.W.F.W. et al., "Noninvasive liposome-mediated gene delivery can correct the ion transport defect in cystic fibrosis mutant mice," Chemical Abstracts, 119:62 (1993) (Abstract 217089w).
Askanas et al., "A New Program for Investigating Adult Human Skeletal Muscle Grown Aneurally in Tissue Culture," Neurology, 25:58-67 (1975).
Badesch et al., "Continuous Intravenous Epoprostenol for Pulmonary Hypertension Due to the Scleroderma Spectrum of Disease, A Randomized, Controlled Trial," Ann. Intern. Med., 132:425-434 (2000).
Baker, R.C., "Pitfalls in Diagnosing Acute Otitis Media," Pediatric Annals, 20:591-593, 596-598 (1991).
Barst et al., "A Comparison of Continuous Intravenous Epoprostenol (Prostacyclin) With Conventional Therapy for Primary Pulmonary Hypertension," N. Eng. J. Med., 334:296-301 (1996).
Berkow, R. (Ed.), The Merck Manual of Diagnosis and Therapy, Sixteenth Edition, Merck Research Laboratories, Division of Merck & Co., Inc., Rahway, N.J. pp. 600-602 (1992).
Berman, S., "Otitis Media in Developing Countries," Pediatrics, 96:126-131 (1995).
Canonico, A.E. et al., "Expression Of A Cmv Promoter Driven Human ?-1 Antitrypsin Gene In Cultured Lung Endothelial Cells And In The Lungs Of Rabbits," Clin. Res., 39(2): 219A (1991).
Carman et al., "A Primary Care Approach to the Patient with Claudication," Am. Fam. Physician, 61:1027-1032 (2000).
Cunningham, M.W., "Pathogenesis of Group A Streptococcal Infections," Clin. Microbiol. 13:470-511 (2000).
Dagan, R. et al., "Treatment Failures in Otitis Media—What Can We Learn?," Ear, Nose and Throat J., 77:16-21 (1998).
Dawson et al., "Cilostazol Has Beneficial Effects in Treatment of Intermittent Claudication," Circulation, 98:678-686 (1998).

(Continued)

Primary Examiner—Christopher R Tate
Assistant Examiner—Randall Winston
(74) Attorney, Agent, or Firm—Marshall, Gerstein & Borun LLP

(57) ABSTRACT

The invention provides a method for administering streptolysin O for treatment of various conditions including connective tissue disorders, reproductive fibroses and conditions mediated by the CD44 receptor. The invention also provides methods for protecting nerve cells from the effects of neurotoxic agents by the administration of streptolysin O.

7 Claims, 1 Drawing Sheet

OTHER PUBLICATIONS

DeGraves et al., "Economics of Mastitis and Mastitis Control," The Veterinary Clinics of North America—Food Animal Practice Update on Bovine Mastitis, 9:421-434 (1993).

Flotte, T.R., et al., "Stable in vivo expression of the cystic fibrosis transmembrane conductance regulator with an adeno-associated virus vector," Chemical Abstracts, 120:229(1994) (Abstract 46918e).

Furth et al., "Gene Transfer into Somatic Tissues by Jet Injection," Analytical Biochemistry, 205:365-368 (1992).

Gardner et al., "Exercise Rehabilitation Programs for the Treatment of Claudication Pain: A Meta Analysis," JAMA, 274:975-980 (1995).

Gent et al., A Randomised, Blinded, Trial of Clopidogrel Versus Aspirin in Patients at Risk of Ischaemic Events (CAPRIE), Lancet, 348:1329-1339 (1996).

Goldhaber et al., "Low-Dose and Subsequent Peripheral Arterial Surgery in the Physicians' Health Study," Lancet, 340:143-145 (1992).

Harrison et al., "Structural Features of Interstitial Lung Disease in Systemic Sclerosis," Am. Rev. Respir. Dis., 144:706-713 (1991).

Hood et al., "Management of Intermittent Claudication with Pentoxifylline: Meta-Analysis of Randomised Controlled Trials," CMAJ, 155:1053-1059 (1996).

International Search Report corresponding to International Patent Application Serial No. PCT/US04/01887 dated Aug. 26, 2004, 2 pages.

Janzon et al., "Prevention of Myocardial Infarction and Stroke in Patients with Intermittent Claudication; Effects of Ticlopidine. Results from STMS, the Swedish Ticlopidine Multicentre Study," J. Intern.Med., 27:301-308 (1990).

Jarrow et al., "Peyronie's Disease and Radical Prostatectomy: Is There A Link?," J. of Urology, 158:1388-1390 (1997).

Karver, S.B., "Otitis Media," Ear, Nose and Throat Disorders, 25:619-632(1998).

Kiessling et al., "Antineuronal Antibodies in Movement Disorders," Pediatrics, 92:39-43 (1993).

Klein, J.O., "Otitis Media," Clinical Infectious Disease, 19:823-833 (1994).

Ledley, F.D., "Non-viral gene therapy," Current Opinion in Biotechnology, 5: 626-636 (1994).

Ledley, F.D. "Nonviral Gene Therapy: The Promise of Genes as Pharmaceutical Products," Human Gene Therapy, 6: 1129-1144 (Sep. 1995).

Marshall, E., "Gene Therapy's Growing Pains," Science, 269: 1050-1055 (1995).

Patterson et al., "Value of a Supervised Exercise Program for the Therapy of Arterial Claudication," J. Vasc. Surg., 25:312-319 (1997).

Razin et al., "Protein Kinases C-$\beta$ and C-e Link the Mast Cell High-Affinity Receptor for IgE to the Expression of c-fos and c-jun," Proc. Natl. Acad. Sci. (USA), 91:7722-7726 (1994).

Rosenfeld, J. et al., "Acute Otitis Media in Children," Primary Care; Clinics in Office Practice, 23(4):677-686(1996).

Rosenfeld, M.A. et al., "Adenovirus-Mediated Transfer of a Recombinant a1-Antitrypsin Gene to the Lung Epithelium in Vivo," Science 252: 431-434(1991).

Ruiz et al., "Streptolysin O and Adherence Synergistically Modulate Proinflammatory Responses of Keratinocytes to Group A Streptococci," Mol. Microbiol. 27:337-346 (1997).

Schrager et al., "Hyaluronic Acid Capsule Modulates M Protein-Mediated Adherence and Acts as a Ligand for Attachment of Group A Streptococcus to CD44 on Human Keratinocytes," J. Clin. Investig. 101:1708-1716 (1998).

Siebold et al., "Recombinant Human Relaxin in the Treatment of Scleroderma, A Randomized, Double-Blind, Placebo-Controlled Trial," Ann. Intern. Med., 132:871-879 (2000).

Silver et al., "Evaluation and Management of Scleroderma Lung Disease Using Bronchoalveolar Lavage," Am. J. Med., 88:470-476 (1990).

Taranta et al., "The Relationship of Sydenham's Chorea to Infection with Group A Stretococci," Am. J. Med., 20:170-175 (1956).

Unemori et al., "Relaxin Modulates Synthesis and Secretion of Procollagenase and Collagen by Human Dermal Fibroblasts," J. Biol. Chem., 265:10681-10685 (1990).

Visa et al., "The Value of Fasciectomy in the Surgical Approach of the Dupuytren's Disease," Romanian Journal of Hand and Reconstructive Microsurgery, 5:9-13 (2000).

Wallaert et al., "Subclinical Pulmonary Involvement in Collagen-Vascular Diseases Assessed by Bronchalveolar Lavage," Am. Rev. Respir. Dis., 133:574-580 (1986).

White et al., "Cyclophosphamide is Associated with Pulmonary Function and Survival Benefit in Patients with Scleroderma and Alveolitis," Ann. Intern. Med., 132:947-954 (2000).

Effect of Streptolysin O on the contraction frequency of nerve muscle co-culture Effect of Streptolysin O after L-Glutamic acid (10mM) intoxication

METHOD OF TREATMENT OF TENDONITIS BY ADMINISTRATION OF STREPTOLYSIN O

RELATED APPLICATION

This application is a continuation-in-part of U.S. Ser. No. 10/764,161, filed Jan. 23, 2004, which is a continuation-in-part of U.S. Ser. No. 10/349,606 filed Jan. 23, 2003, now U.S. Pat. No. 6,998,121, the disclosures of which are hereby incorporated by reference in their entireties.

FIELD OF THE INVENTION

The present invention relates to methods for treatment of various conditions by the administration of streptolysin O including connective tissue disorders, reproductive fibroses and conditions mediated by the CD44 receptor. The invention also provides methods for protecting nerve cells from the effects of neurotoxic agents by the administration of streptolysin O. The invention further provides methods of alleviating symptoms of a connective tissue disorder, such as tendonitis, by the administration of streptolysin O.

BACKGROUND OF THE INVENTION

Connective tissue is the material between the cells of the body that gives tissues form and strength. This "cellular glue" is also involved in delivering nutrients to the tissue, and in the special functioning of certain tissues. Connective tissue is made up of dozens of proteins, including collagens, proteoglycans, and glycoproteins. The combination of these proteins can vary between tissues. The genes that encode these proteins can harbor defects or mutations, which can affect the functioning of certain properties of connective tissue in selected tissues. As described below, there are a number of different disease states where connective tissue play an important role in the pathological manifestations of the particular disease including Dupuytren's contracture, scleroderma, Peyronie's disease, claudication due to peripheral arterial disease and mastitis in animals.

According to one of its aspects, the present invention relates to methods for treatment of connective tissue disorders including Dupuytren's contracture, scleroderma, Peyronie's disease, and lower limb claudication. These diseases take an enormous toll on people's ability to work, perform physical and sexual activity, maintain normal living standards, and perform everyday activities. In addition, post chronic mastitis infections in bovines have huge economic implications on the viability of livestock and the food supply, specifically the dairy industry.

Peripheral arterial disease (PAD) involves damage to or blockage of the blood vessels distant from the heart (usually in the arms and the legs) and includes several clinical syndromes in the extremities characterized by pain, inflammation, and ischemic damage to soft tissues from partial or complete occlusion of major arteries. The most characteristic symptom of PAD is intermittent claudication, which is described as cramping, aching, and numbness of the extremities induced by exercise. Intermittent claudication subsides by ending the exercise regiment. The symptoms of claudication result from atherosclerosis, which is a condition where plaque consisting of cholesterol, fats, calcium, and fibrin (blood clotting agent) build up on the inside of the artery wall. The artery wall consists of three layers: a layer of connective tissue, a second layer of smooth muscle cells and elastic connective tissue, and a third layer of endothelial cells. Damage to these cells leads to thrombocyte adhesion, aggregation, and formation of thrombi or intima in the arterial wall. This formation allows monocytes to stick to the arterial wall and maturate into macrophages, while recruiting LDL cholesterol to create a foam cell formation or fatty streaks. This interruption in the arterial endothelial lining causes platelets to become activated and recruit smooth medial muscle cells into the initma leading to connective tissue proliferation and lipid uptake. This cycle of inflammation and proliferation of connective tissue in the arterial wall of the blood vessel leads to narrowing of the arterial lumen, restricting blood flow.

The risk factors for atherosclerosis in the peripheral arteries of the legs and arms are the same as those for atherosclerosis in the coronary arteries. Smoking, diabetes, high blood pressure, and high cholesterol lead to the development of plaque. Most people with atherosclerosis in the leg arteries have no symptoms because the body develops small blood vessels (collateral vessels) around the blockage. With sustained activity, the collateral vessels are unable to supply enough oxygen to the leg's muscles and therefore, the pain is associated in the calf, thigh or buttocks muscles. In more advanced claudication, pain can occur even while one is at rest. If this symptom is left untreated, the lack of circulation may result in sores on the legs and feet, and the tissue can become gangrenous, requiring amputation.

Claudication is often a sign of atherosclerosis of both the coronary and carotid arteries. In treating atherosclerotic diseases, physicians should focus on evaluation, risk factor modification (quitting smoking and reducing cholesterol), and exercise (stimulate carotid arteries and condition muscles) (see Carmen et al., *Am Fam. Physician* 61:1027-1034 (2000); Gardner et al., *JAMA* 274:975-980 (1995); Patterson et al., *J. Vasc. Surg.* 25:312-319 (1997)). Antiplatelet agents, which prevent the recruiting activities of platelet cells, such as aspirin, ticlopidine, or clopidogrel, reduce the risk of vascular death, myocardial infarction, and stroke as much as 24% (see Goldhaber et al., *Lancet* 340:143-145 (1992); Janzon et al., *J. Intern. Med.* 227:301-308 (1990); *Lancet* 348:1329-1339 (1996)). The combination of exercise and the drug pentoxifylline appears to reduce claudication (Hood et al., *CMAJ* 155:1053-1059 (1996)). The drug, Cilostazol, a phosphodiesterase inhibitor that suppresses platelet aggregation and arterial vasodilator, increases the amount and quality of exercising a patient can perform to overcome claudication (Dawson et al., *Circulation* 98:678-686 (1998)). Although these medical measures show some improvement of claudication, there remains a need in the art for methods to better treat peripheral arterial disease.

Dupuytren's contracture is a painless thickening and contracture of tissue beneath the skin on the palm of the hand. The cause of the contracture is unknown, but minor trauma and genetic predisposition may play a role. One or both hands may be affected. The ring finger is affected most often, followed by the little, middle and index finger. A small, painless nodule develops in the connective tissue and eventually develops into a cord-like band. Gradually, other nodules may develop and extend a contracture across the first joint into the finger. The overlying skin begins to pucker, and rough cords of tissue extend into the finger. As the process continues, these cords tighten and pull the finger in toward the palm. The ring finger is usually affected first, followed by the little, long and index fingers. The problem is not pain, but the restriction of motion and the deformity it causes. The progress of the disease is often sporadic and unpredictable. Exactly what triggers the formation of nodules and cords is unknown. As the disease progresses, the diseased nodules wraps itself around and between the normal tissue.

The incidence increases after the age of 40, and men are affected more often than women. Interestingly, the risk factors are associated with alcoholism, epilepsy, pulmonary tuberculosis, diabetes, and liver disease. Treatment for this disease can include exercises to stretch the diseased tissue, warm water baths, or splints. Often, these measures only slow the contracture, but do not cure the contracture. If the contracture continues, surgery may be performed to release the contracture, depending upon the severity of the condition. Several techniques including fasciectomy, dermofasciectomy, fasciotomy, and amputation are used. Fasciectomy is a corrective surgery performed by removing the fascia tissue and stitching up the wound in a zig-zag manner (See Visa et al., *Romanian Journal of Hand and Reconstructive Microsurgy* 5:9-13 (2000)). Dermofasciectomy is a corrective procedure of an advanced state of Dupuytren's contracture, where the skin and the fascia bands and nodules are removed. The removed skin is replaced by a skin graft. Fasciotomy is a medical procedure for elderly patients unfit for complicated surgery where the bands are cut. Finally, in rare cases, fingers in which the bands have returned many times and previous nerve and tissue damage exist, amputation of the finger is an option. While surgery usually restores normal movement to the fingers, the disease can reoccur following surgery and the risk of nerve damage increases after each surgery. Therefore, there remains a need for a less drastic method for treating Dupuytren's contracture.

Peyronie's disease is a disorder of the connective tissue within the penis that can cause curvature during erection. The disease is characterized by a plaque, or a hard lump, that forms in the erectile tissue of the penis. It begins as a localized inflammation and can then mature into a hardened scar. The cause of Peyronie's disease can be attributed to the septum connective tissue, which lines the inner membrane of each erectile cylinder that runs the length of the penis and attaches at the top and bottom of the penis. If the penis is abnormally squeezed or flexed, the area where the septum attaches to the elastic fibers may over-stretch, injuring the lining of the erectile chamber and rupturing small blood vessels. In older men, diminished elasticity, disease of the arteries, diabetes, or radical prostatectomy further increase the chance of injury. In fact, Peyronie's disease is diagnosed in only 26 out of 100,000 men each year; however, the ratio increases to 3 out of 64 patients who develop Peyronie's disease after a radical prostatectomy (Jarrow et al., *J. of Urology* 158:1388-1390 (1997)).

Men with Peyronie's disease usually seek medical attention because of painful erections or difficulty with intercourse. The goal of any treatment is to keep the Peyronie's patient sexually active. Providing education about the disease and its course is often all that is required. There is no strong evidence that any treatments other than surgery are effective. Experts usually recommend surgery only in long-term cases where the disease has stabilized and where the deformity prevents intercourse. The two most common surgical methods are removal or expansion of the plaque followed by a placement of a patch of skin or artificial material and removal of pinching tissue from the side of the penis. Both procedures have the disadvantage of side effects including loss of erectile function or shortening of the erect penis. Often, the plaques of Peyronie's disease shrinks or disappears without treatment over a 6-15 month period, and thus, medical experts suggest waiting 1 to 2 years before attempting to correct it surgically. Spontaneous improvement in the disease is seen in 60-70% of patients.

Simple medical treatments have not been clinically proven. Some researchers have given men with Peyronie's disease vitamin E orally in small-scale studies, but these studies have proven inconclusive. Also, similar inconclusive success has been attributed to oral application of para-amino benzoate, a substance belonging to the family of B-complex molecules. Injection treatment with agents such as dimethyl sulfoxide, steroids, and calcium channel blockers directly into the plaques is used by some doctors, but none of these techniques have produced convincing results. The only medical treatment proven to be effective is Tamoxifen, which can relieve the pain and limit any subsequent bending of the penis. The disadvantage of Tamoxifen is that Peyronie's disease must be diagnosed early for the most effective use of the drug and therefore, there remains a desire in the art for methods for the treatment and prevention of Peyronie's disease.

Scleroderma is an autoimmune disease of the connective tissue, which affects many body systems such as the gastrointestinal tract, the respiratory, renal, cardiovascular, and genitourinary systems, but is primarily characterized by thickening and tightening of the skin. This disease may either be visible, as when the skin is affected, or invisible, as when only internal organs are involved, but is usually a highly-individualized disease wherein its involvement may range from mild symptoms to life-threatening symptoms. The symptoms result from progressive tissue fibrosis and occlusion of the microvasculature by excessive production and deposition of types I and II collagens. Other macromolecules found in connective tissue (e.g., glycosaminoglycans, tenascin, fibronectin) increase in production due to inflammation of the area experiencing fibrosis. The vascular alternations show a predilection for affecting the small arteries, arterioles, and capillaries. The small vessel cytoskeleton is affected by structural defects that lead to collapse. Next, the tight junctions become altered and are no longer functional, allowing the endothelium to slip into the vessel lumen.

An estimated 300,000 persons in the United States have scleroderma with more women (4 times more) than men developing the disease usually between the ages of 20 to 50. Symptoms of scleroderma include one or more of the following: Raynaud's Phenomenon (abnormal sensitivity to cold in the extremities), swelling of the hands and feet, pain and stiffness of the joints, thickening of the skin, joint contractures, digestive system and gastrointestinal tract problems, Sjogren's Syndrome (dry mucus membranes), oral, facial and dental problems, kidney, heart, and lung involvement, and non-specific symptoms such as extreme fatigue, generalized weakness, weight loss, and vague aching of muscles, joints and bones. The most serious side effect of scleroderma is pulmonary hypertension, and its complications are the most frequent causes of mortality. For example, the lungs are affected in 70-80% of patients, and develop either fibrosis or change in the blood vessels, which leads to increased pressure in the pulmonary arteries (Harrison et al., *Am. Rev. Respir. Dis.* 144:706-713 (1991); Silver et al., *Am. J. Med.* 88:470-476 (1990)). The fibrosis usually starts with an increase in lung fiber density near the posterior (back) regions of the lungs. Later stages of fibrosis are characterized by the emergence of a network of fibrous lines. These fibrous lines eventually develop into regions containing large numbers of small cysts. The end-stage effect is sometimes referred to as "honeycombing" and is non-reversible (Wallaert et al., *Am. Rev. Respir. Dis.* 133:574-580 (1986)).

The goal for treating scleroderma is to prevent further complications (i.e. fibrosis) and reduce morbidity if complications exist. Primary treatment consists of inhibiting the immune system alterations, which may be responsible for the wide variety of systemic morbidity associated with this disease. Skin thickening can be treated with D-penicillamine and methotrexate, which both increases the effects of immunosuppressants and slows down the formation of collagen. The experimental drug relaxin has also shown promise reducing the extent and severity of skin thickening in patients with diffuse scleroderma (Seibold et al., *Ann. Intern. Med.* 132: 871-879 (2000)). Relaxin attenuates the actions of profibrotic cytokines including transforming growth factor-β and interleukin-1β, and increases secretion of dermal fibroblast collagenase, while reducing levels of tissue inhibitor of metalloproteinase (Unemori et al., *J. Biol. Chem.* 265:10681-10685 (1990)). Raynaud phenomenon can be treated with calcium blockers or topical nitrates. Gastrointestinal symptoms may be treated with antacids, pump inhibitors, and laxatives. More severe complications, like fibrosis in the lungs or pulmonary hypertension, require more drastic measures. For example, scleroderma and alveolitis (hypersensitive inflammation of alveolar cells in the lung) can cause severe damage to lung tissues. Treatment with experimental drugs such as cyclophosphamide work to inhibit inflammation, but is not effective against only scleroderma in the lungs. Rather, both sets of symptoms are required (White et al., *Ann. Intern Med.* 132: 947-954 (2000)). Pulmonary hypertension is a relatively common complication of systemic sclerosis with a lack of viable treatment options and a high mortality rate. In light of these factors, the use of intravenous epoprostenol has shown some promise (Badesch et al., *Ann. Intern. Med.* 132:425-434 (2000)), but may have limited applicability due to possible acute and potentially fatal side effects such as pulmonary edema in patients suffering with veno-occlusive disease as well as scleroderma (Barst et al., *N. Eng. J. Med.* 334:296-301 (1996)). Many of these treatments are in their experimental stages, and the current treatments for the various scleroderma complications either cause the patients to experience severe side effects, place them at risks for further complications or require a unique set of symptoms to provide adequate treatment. Thus, there remains a need in the art for improved methods for treating scleroderma.

Of interest is a study which reports that streptolysin O has been shown to modulate or reduce the excessive production of collagen in two murine models of scleroderma (Mamber et al., Nonlinear. Biol. Toxicol. Med., 2:67-87, 2004).

Post chronic mastitis infection is a connective tissue disorder that can prevent adequate lactation of bovines. Mastitis is an inflammation of the udder that affects a high proportion of dairy cows throughout the world. There are three major types of mastitis, corresponding to three distinct stages of development. Acute mastitis is generally characterized by redness, heat, pain, hardness or swelling accompanied by fever, a loss of appetite, and lower milk production. There are two stages during acute mastitis including (1) the inflammatory stage where there is no infection and few to no lumps in the teats; (2) the infection stage where pus is generated and lumps begin to form. Bacteria such as *Escherichia coli, Streptococcus dysgalactiae*, coagulase-negative staphylococci, *Staphylococcus aureus, Streptococcus uberis*, colorless algae and corneybacterium can cause the initial infection via numerous vectors such as flies, flowing water, standing water, water tanks, water runoff from silage, well water, manure, teat dip containers, milking machine liners, teat end swabs and feed troughs. These bacteria are able to invade the mammary gland, multiply therein, and produce harmful substances that result in an inflammatory response. Once infection begins, the teats can become so infected that the milk first becomes yellow and then watery. After infection, chronic mastitis can occur which is the after-effect of repeated bouts of mastitis at the level of the teat where humps, lesions, hardenings, damaged teats, lost quarters, nodularthelitis, and a drop in milk production occur.

The focus of treatment is dependent upon the level of infection and how many repeat occurrences of mastitis have occurred. It is important to diagnose mastitis early in the infection. Chronic mastitis is the most critical to prevent. Animals with chronic mastitis often acquire permanent damage to the teat and the bovine loses productivity and is unable to release milk at a sufficient level from the damaged teat.

Mastitis is difficult to control since several bacteria have the ability to infect the udder. Even well managed dairy herds that utilized the most recent and most effective mastitis control measures witness a high rate of infection in the first 90 days of lactation (Schrick et al., *Department of Animal Science Annual Report*, The University of Tennessee, Knoxville, in press). Mastitis has been described as the most economically imposing disease facing dairy producers in the United States, costing an estimated $2 billion annually (DeGraves and Fetrow, *The Veterinary Clinics of North America-Food Animal Practice Update on Bovine Mastitis* 9:421-434 (1993)). Thus, there remains in the art the need for treatment that will allow bovines to continue to exhibit productive milk even after damage to the udder has occurred due to complications from chronic mastitis.

Reproductive fibrosis in the form of fibroids (noncancerous growths) affects the reproductive organs of female mammals, most notably the uterus and the fallopian tubes. Fibroids can grow inside, within the muscle wall and on the outside surface of the uterus. Reproductive fibrosis can result in various symptoms including pain, bleeding, urinary tract, bladder and kidney infection, infertility and difficulties with pregnancy. Reproductive fibroids do not occur prior to puberty and frequently cease having symptoms after the conclusion of menopause. Fibroids that do not cause symptoms or that cause only minor symptoms usually do not require treatment. Reproductive fibroses that cause more severe symptoms are treated with medications such as oral contraceptives or gonadotropin-releasing hormone agonists (GnRH-As). Non-surgical treatments such as uterine fibroid embolization which is a radiological procedure may be carried out to treat fibroids. Further, surgical treatments such as myomectomy (which is intended to retain fertility) or hysterectomy (which will not retain fertility) may be carried out. Despite these therapies, there remains a desire in the art for additional options for treatment of reproductive fibroses.

Of interest to the present invention is the CD44 family of surface receptors which regulate various cellular activities. The CD44 receptor protein is a transmembrane glycoprotein with an approximate molecular weight of about 37 kD and has a role in matrix adhesion lymphocyte activation to the basement membrane and in the maintenance of epithelial cell polarity. As such, the CD44 receptor protein is also known as the lymph node homing receptor and is homologous to the "cartilage link protein." Hyaluronic acid (HA) is one of its ligands. Altered expression of the CD44 receptor is believed to be associated with tumor progression and metastases in various cancers. In addition, degradation of HA may play a critical role in promoting the formation of scar tissue in the damaged nervous system that inhibits axonal regeneration following injury to the brain or spinal cord. In contrast, the accumulation of high molecular weight forms of HA may contribute to the pathogenesis of various neurodegenerative diseases, including multiple sclerosis and Alzheimer's disease. Also of interest to the present invention is the observation that the CD44 receptor on fibrous astrocytes appears to be up-regulated in Multiple Sclerosis. Accordingly, there exists a desire for agents and methods to intervene with the biological activities of the CD44 receptor as well as the effects of hyaluronic acid on that receptor. Further, there also exists a need for neuroprotective agents to protect neurons against both natural and synthetic neurotoxic agents in the environment and which result in vivo as a result of metabolic processes.

Streptolysin O is one of a group of filterable hemolysins derived from Group A beta-hemolytic streptococci. Specifically, streptolysin O is a 60-kD peptide, which is hemolytic in its reduced state, but is inactivated upon oxidation. Group A streptococci produce streptolysin O. Streptolysin O is used in the art generally as an analytical reagent for permeabilizing cells (e.g. Razin et al., *Proc. Nat'l. Acad. Sci.* (*USA*) 91:7722-7726 (1994).

It is thought that induction of a pro-inflammatory response in keratinocytes (skin cells) is associated with adherence of streptococci and their production of streptolysin O (Ruiz et al., *Mol. Microbiol.* 27:337-346 (1997); Cunningham, M. W., *Clin. Microbiol.* 13:470-511 (2000)). Specifically, the hyaluronic acid capsule of group A streptococci may be an important adherence factor since it binds to CD44 on epithelial cells (Schrager et al., *J. Clin. Investig.* 101:1708-1716 (1998)). Streptolysin O may also interact with CD-44 receptors on keratinocytes and dissolve collagen to allow streptococci to get in the blood stream. It has recently been reported that streptolysin O enhances keratinocyte migration and proliferation and promotes skin organ culture wound healing in vitro (Tomic-Canic et al., Wound Rep. Reg., 15:71-79, 2007).

The pharmacological effects of low levels of ML-05, a modified form of the hemolytic and cytotoxic streptolysin O, on keratinocyte growth and up-regulation of CD44 were characterized in previous in vitro studies (Mamber et al., Nonlinear. Biol. Toxicol. Med., 2:67-87, 2004). Briefly, ML-05 appeared to decrease skin collagen levels in two in vitro models of collagen disorders, the tight skin mouse (Tsk) model of scleroderma, and the bleomycin-induced mouse skin fibrosis model.

It has been reported that prior infection with a Group A beta-hemolytic streptococcus is linked to subsequent development of movement disorders. Taranta, et al., Am. J. Med., 20: 170-175 (1956). Moreover, there are reports that patients having Group A beta-hemolytic streptococcal infections produce antibodies against their own neural tissue and that such antibodies are stimulated by the streptococcal infection. Kiessling, et al., Pediatrics, 92:39-43 (1993). Interestingly, patients with central nervous system deficits which result in impaired movement have high anti-streptolysin O antibody titers and those antibodies cross-react with myelin basic protein, a suspected causative agent in multiple sclerosis.

Tendonitis is perhaps one of the most frustrating athletic injuries involving the lower leg of a horse. Tendonitis is defined as the inflammation of the tendon and tendon-muscle attachments. A "bowed tendon" is caused by an injury to the superficial digital flexor tendon, the tendon lying closest to the skin on the abck portion of the leg between the carpus (knee) and the fetlock (ankle). Tendonitis usually results from a severe strain or hyperextension of this tendon during excessive loading during work. Poor footing in the arena, excessive pastern slope, improper shoeing, and tight fitting leg wraps may place extra stresses on this tendon.

Clinical signs include, diffuse swelling on the back of the leg, heat, pain on palpation, and varying degrees of lameness depending on the severity of the injury. Tendon injuries can vary from mild inflammation of the surrounding tendon structures, to more severe tears of the tendon fibers, to partial or complete rupture. An aggressive approach to therapy may make the difference in the horse's ability to return to its previous level of performance. Inappropriate therapy may lead to chronic lameness problems due to re-injury of the tendon. Surgical options include: ultrasound guided tendon puncture and/or superior check ligament desomtomy. The goal of medical treatment is to keep the inflammatory response to a minimum. Ideally the aim is to limit the amount of inflammation to that necessary to repair the injury and keep the inflammation from affecting the remaining normal tendon (reduce unwanted scar tissue). Current therapy includes one or more of the following: cold therapy (application of cold water or ice four to six times a day); bandaging to provide counter pressure against the swelling; stall rest; and anti-inflammatory medication.

The disclosures of co-owned U.S. Pat. Nos. 5,576,289 and 5,736,508 disclosures are hereby incorporated by reference. U.S. Pat. No. 5,576,289 discloses the use of streptolysin O in methods for treating disease states characterized by motor deficit including multiple sclerosis and autism. U.S. Pat. No. 5,736,508 discloses the use of streptolysin O in methods for treating scarring. No disclosure, however, is made of an utility wherein streptolysin O is used to treat connective tissue disorders such as tonditinis, Dupuytren's contracture, scleroderma, Peyronie's disease, mastitis in animals, and claudication due to peripheral arterial disease, that streptolysin O has direct neuroprotective effects or therapeutic effects on reproductive fibroses or that it has the effect of inhibiting hyaluronic acid binding to CD44 receptors or otherwise inhibits CD44 mediated processes.

SUMMARY OF THE INVENTION

According to one of its aspects, the present invention provides methods for treating connective tissue disorders by administering streptolysin O. Specifically, the invention provides methods for alleviating symptoms of a connective tissue disorder such as Dupuytren's contracture, scleroderma, Peyronie's disease, mastitis in animals, and claudication due to peripheral arterial disease by administering to a patient in need thereof, streptolysin O in an amount effective to treat one or more symptoms of the connective tissue disorder. As used herein, streptolysin O shall include the streptolysin O molecule as well as active fractions, analogs and derivatives thereof that maintain the biological activity of streptolysin O such as the ability to interact with the CD44 receptor or inhibit CD44 receptor mediated processes.

According to this aspect, the invention comprises administration to a patient suffering from a connective tissue disorder such as tendonitis, Dupuytren's contracture, scleroderma, Peyronie's disease, mastitis in animals, and claudication due to peripheral arterial disease, an effective amount of streptolysin O. In one aspect, the tendonitis is equine tendonitis. The precise dose will vary among patients and may readily be determined by those of ordinary skill in the art. Nevertheless, streptolysin O is preferably administered in a amount ranging from about 0.0032 to 50 units (2 units/0.05 ml) per day and is preferably formulated in a liquid vehicle and provided at a concentration of approximately 4 units as a single drop. A single drop of streptolysin O is within the range of 0.05 to 10 units. More preferably, a drop of streptolysin O is in the amount of 2 units as a single drop. Streptolysin O is more preferably administered in an amount ranging from about 0.01 to 10 units per day or even more preferably administered in an amount ranging from about 0.1 to 8 units per day. A preferred route of administration is sublingually, but other routes including bucal, oral drench, anal, vaginal, nasal, intralesional, subcutaneous, intradermal, intramuscular, intrathecal, intravenous, inhalation or topical, by capsules, tablets, spray, topical lotions, creams, patches, or by intradermal or dermal punctures are expected to work.

The invention also provides a pharmaceutical composition of streptolysin O and active fractions thereof for administering to a subject, or patient for alleviating symptoms of a connective tissue disorder such as tendonitis, Dupuytren's contracture, scleroderma, Peyronie's disease, claudication due to peripheral arterial disease, and mastitis wherein the streptolysin O is in an amount effective to treat one or more symptoms of said connective tissue disorder in combination with pharmaceutically-acceptable excipients. In one aspect, the tendonitis is equine tendonitis. Streptolysin O may be formulated in a number of pharmaceutically-acceptable excipients including, but not limited to, water, saline, albumin, dextrose or any other pharmaceutically acceptable excipient known in the art. The streptolysin O is preferably administered in a dosage amount ranging from about 0.0032 to 50 units (2 units/0.05 ml) per day and is preferably formulated in a liquid vehicle and provided at a concentration of approximately 4 units as a single drop. A single drop of streptolysin O is within the range of 0.05 to 10 units. More preferably, a drop of streptolysin O comprises about 2 units as a single drop. Streptolysin O is more preferably administered in an amount ranging from about 0.01 to 10 units per day or even more preferably administered in an amount ranging from about 0.1 to 8 units per day. A preferred route of administration is sublingually, but other routes, such as bucal, oral drench, subcutaneous, intradermal, intramuscular, intrathecal, intravenous, inhalation or topical, are expected to work.

According to a further aspect of the invention, methods for alleviating symptoms of fibrotic conditions, such as but not limited to fibrosis of the kidney, liver, heart, lung, pancreas and other organs and further including reproductive fibrosis conditions such as uterine fibrosis and fallopian tube fibrosis are provided. The methods comprise administering to a subject in need thereof, streptolysin O and active fractions thereof in an amount effective to treat one or more symptoms of the reproductive fibrosis including infertility and menstrual irregularities. The method may be applied to all types of mammalian subjects and in particular to equine and human subjects. Those of ordinary skill in the art can readily determine appropriate dosages for administration based on the therapy to be effected, the size of the subject and the mode of administration. Nevertheless, preferred dosages include those wherein the streptolysin O is administered at a dosage from about 0.0032 units to about 50 units and more preferably from about 0.05 units to about 10 units and most preferably from about 0.01 units to about 1.0 unit.

Streptolysin O may be formulated for administration to subjects suffering from reproductive fibroses in a number of pharmaceutically-acceptable excipients including, but not limited to, water, saline, albumin, dextrose or any other pharmaceutically acceptable excipient known in the art. The streptolysin O is preferably administered in a dosage amount ranging from about 0.0032 to 50 units (2 units/0.05 ml) per day and is preferably formulated in a liquid vehicle and provided at a concentration of approximately 4 units as a single drop. A single drop of streptolysin O is within the range of 0.05 to 10 units. More preferably, a drop of streptolysin O is in the amount of 2 units as a single drop. Streptolysin O is more preferably administered in an amount ranging from about 0.01 to 10 units per day or even more preferably administered in an amount ranging from about 0.1 to 8 units per day. A preferred route of human administration is sublingually, but other routes, such as bucal, oral drench, subcutaneous, intradermal, intramuscular, intrathecal, intravenous, inhalation or topical, are expected to work. For non-human animals such as horses, a preferred mode of administration is by subcutaneous administration at a dosage of 2 units per dose (0.2 cc).

Also provided by the invention are methods for protecting subjects from the effects of neurotoxic agents and conditions comprising the step of administering neuroprotective amounts of streptolysin O. Neurotoxic agents are those capable of damaging or destroying neurons and include natural and synthetic agents present in the environment and further include natural metabolic products having neurotoxic properties. Neurotoxic conditions are not limited to those of a chemical origin and include damaging radiation and thermal conditions. In addition, the administration of streptolysin O may also be beneficial in repairing preexisting damage caused to neurons.

Streptolysin O may be administered for its neuroprotective effects to mammals generally and humans in particular. According to such methods the streptolysin O may be administered by a mode selected from the group consisting of sublingual, bucal, oral drench, subcutaneous, intradermal, intravenous, intramuscular, intrathecal, inhalation, and topical. Those of ordinary skill in the art can readily determine appropriate dosages for administration based on the therapy to be effected, the size of the subject and the mode of administration. Nevertheless, preferred dosages include those wherein the streptolysin O is administered at a dosage from about 0.0032 units to about 50 units and more preferably from about 0.05 units to about 10 units and most preferably from about 0.01 units to about 1.0 unit.

Also provided by the invention are methods for inhibiting CD44 receptor mediated processes comprising administering streptolysin O to cells expressing the CD44 receptor in amounts effective to inhibit said CD44 receptor mediated processes including, but not limited to, mobilization and orientation of hyaluronic acid generally and as involved in wound healing. Other CD44 mediated processes which may be susceptible to treatment with streptolysin O according to the invention include endometrial hyperplasia/carcinomas, orapharyngeal squamous cell carcinoma, breast carcinoma and panbronchiolitis. In particular, the invention provides methods of inhibiting hyaluronic acid binding to the CD44 receptor, which method provides administering streptolysin O to cells expressing the CD44 receptor in an amount effective to inhibit said hyaluronic acid binding. The methods may be carried out by administration of streptolysin O to subjects in which it is desired to inhibit CD44 receptor mediated processes including human subjects. According to such methods the streptolysin O may be administered by a mode selected from the group consisting of sublingual, bucal, oral drench, subcutaneous, intradermal, intravenous, intramuscular, intrathecal, inhalation, and topical. Those of ordinary skill in the art can readily determine appropriate dosages for administration based on the therapy to be effected, the size of the subject and the mode of administration. Nevertheless, preferred dosages include those wherein the streptolysin O is administered at a dosage from about 0.0032 units to about 50 units and more preferably from about 0.05 units to about 10 units and most preferably from about 0.01 units to about 1.0 unit.

DETAILED DESCRIPTION

Figure 1:
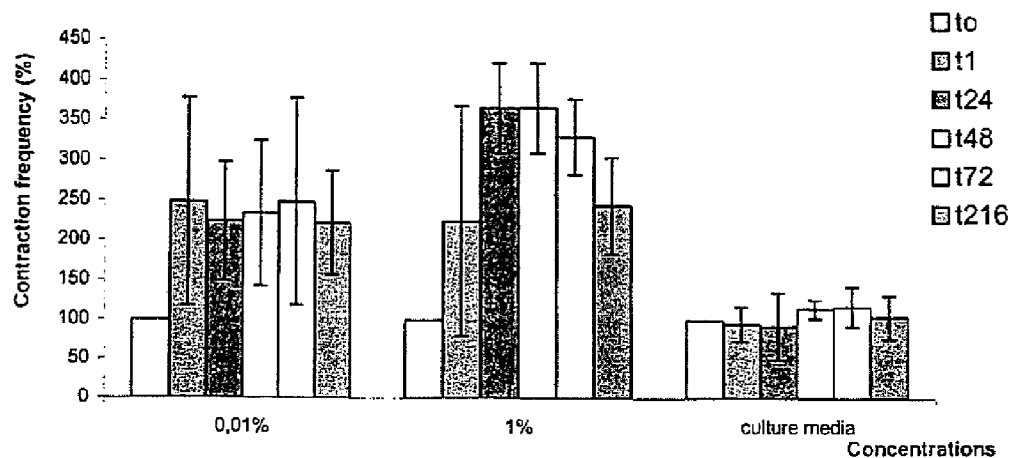
FIG. 1 depicts the effects of streptolysin O on the contraction frequency in a nerve muscle co-culture in a glutamate intoxication model.

The present invention provides methods for treating patients with symptoms of connective tissue disorders by any variety of modes of administration including, but not limited to, bucal, oral drench, anal, vaginal, nasal, intralesional, subcutaneous, intradermal, intramuscular, intrathecal, intravenous, inhalation or topical administration of a small amount of streptolysin O in a pharmaceutically acceptable excipient including water, saline, albumin, and dextrose. Internal organs with the potential for fibrotic conditions that can be treated by the methods of the invention include respiratory: lung, larynx, pharynx, nasal, sinisoids, Eustachian tubes, bronchioles (COPD, emphysema); gastric intestinal: intestinal adhesions, intestinal fibroids, "visceral", esophagus, liver, alimentary canal, hemorrhoids, rectal scarring, gall bladder ducts; circulatory and cardiac system heart, pericardia (pericarditis), ischemia, varicose veins, angina pectoralis, pancreas, lymph nodes; genital urinary kidneys, uterus and endometrium, polyps (vaginal and urethral,), penis, vagina, fallopian tubes, urethra, bladder, prostate, ovaries; nervous: spinal cord, peripheral nerves, eyes, epidural and subdura (brain coverings), otic chambers, integument skin ulcers, scars, burns, acne cysts, other cysts, scleroderma; muscular/skeletal: ligaments and joints, skeletal muscle. Specifically, the present invention provides methods for treating Dupuytren's contracture including, but not limited to, treating the symptoms of thickening and contracture of the tissue beneath the skin of the palm of the hand and the limited everyday function with the hands.

The present invention also provides methods for treating claudications due to peripheral arterial disease by administration of a small amount of streptolysin O. Methods of the invention are also useful for treating symptoms of peripheral arterial disease including, but not limited to, the intermittent claudication symptoms such as cramping, aching, numbness, lack of circulation, and/or pain of the extremities.

The present invention also provides methods for treating patients with symptoms of Peyronie's Disease by administration of a small amount of streptolysin O. Methods of the invention are also useful for treating Peyronie's disease complications sufficient to treat symptoms of Peyronie's Disease including, but not limited to, painful erections or difficulty with intercourse.

The present invention also provides methods for treating patients with symptoms of scleroderma by administration of a small amount of streptolysin O. Methods of the invention are also useful for treating scleroderma complications, including, but not limited to, Raynaud's Phenomenon, swelling of the hands and feet, pain and stiffness of the joints, thickening of the skin, joint contracture, digestive and gastrointestinal tract problems, Sjogen's Syndrome, facial and dental problems, kidney disease, heart disease, lung disease, extreme fatigue, generalized weakness, weight loss, vague aching of muscles, joints, and bones, and pulmonary hypertension.

The present invention also provides methods for treating symptoms of chronic mastitis in bovines by administration of a small amount of streptolysin O. Methods of the invention are also useful for treating mastitis complications characterized by redness, heat, pain, hardness or swelling accompanied by fever, a loss of appetite, and lower milk production of the bovine.

The invention also provides methods for treating symptoms of reproductive fibrosis including uterine and fallopian tube fibroses by administration of effective amounts of streptolysin O.

The present invention also provides methods for treating tendonitis by administration of streptolysin O. In one aspect, the tendonitis is equine tendonitis. Methods of the invention are also useful for alleviating symptoms associated with equine tendonitis including, but not limited to, swelling, heat, and pain. If the tendonitis is more severe, the injury is usually accompanied by moderate lameness (2-3 on a scale of 5) with obvious swelling.

The invention further provides neuroprotective methods for prevention of the negative effects of neurotoxic agents on nerve cells by administration of effective amounts of streptolysin O.

Further, the invention provides methods for the intervention in CD44 receptor mediated conditions comprising the administration of streptolysin O to cells expressing the CD44 receptor in amounts effective to inhibit those processes. Also provided are methods of inhibiting hyaluronic acid binding to the CD44 receptor comprising administering streptolysin O to cells expressing the CD44 receptor in an amount effective to inhibit such hyaluronic acid binding to the CD44 receptor.

The following Examples illustrate the methods of the invention with respect to treatment of psychological conditions, and, in particular, with respect to preferred methods of treating connective tissue disorders. In particular, streptolysin O was used to treat these various psychological disorders. The streptolysin O was purchased from Sigma Chemicals, St. Louis, Mo. Numerous improvements and further aspects of the invention are apparent to the skilled artisan upon consideration of the Examples, which follows.

The following examples illustrate various aspects of the invention. Examples 1-8 illustrate the methods of the invention with respect to treatment of connective tissue disorders, including example 8 which illustrates a method of treating bovine mastitis. Examples 9 and 10 illustrate methods of administering streptolysin O to subjects suffering from reproductive fibrosis. Examples 11 and 12 illustrate methods of protecting nerve cells from the effects of neurotoxic agents. Example 13 shows the results of competitive inhibition assays carried out between hyaluronic acid and streptolysin O on human keratinocyte CD44 receptors. Examples 14-16 illustrate methods of administering streptolysin O to subjects suffering from tendonitis.

Example 1

An 85-year old female patient suffered from calf pain due to peripheral arterial disease. She began treatment with one drop (2 units/0.05 ml) of streptolysin O two to four times daily by sublingual administration. Before treatment, she could only walk three minutes without experiencing pain in her calf. With treatment, she has been able to walk nine minutes without pain in her calf.

Example 2

An 80-year old female patient suffered from lower extremity pain due to peripheral arterial disease on her right side. She began a treatment regimen of one drop (2 units/0.05 ml) of streptolysin O four times daily by sublingual administration. With this treatment regimen, her pain has been relieved.

Example 3

A 72-year old male was diagnosed with lower leg pain due to peripheral arterial disease by his physician. He began treatment with streptolysin O at a rate and amount of one (2 units/0.05 ml) drop, four times daily by sublingual administration. The treatment regimen has significantly decreased the leg pain and further improved his energy, ability to work, and improved his overall quality of life.

Example 4

A 67-year old male was diagnosed with Dupuytren's contracture in one hand. He began treatment with streptolysin O at a rate and amount of one (2 units/0.05 ml) drop, four times daily by sublingual administration. After 14 days of treatment, the symptoms of the disease progressively reversed with each new treatment.

Example 5

A 64-year old male was diagnosed with Dupuytren's contracture in both hands by his physician. He began treatment with streptolysin O at a rate and amount of one (2 units/0.05 ml) drop, four times daily by sublingual administration. After 14 days of treatment, the symptoms of the disease progressively reversed in both hands with each new treatment.

Example 6

A 57-year old male patient was diagnosed with Peyronie's disease by his physician. He began treatment with streptolysin O at a rate and amount of one (2 units/0.05 ml) drop, three times daily by sublingual administration. After 30 days of treatment, improvements in the contracture of his penis were noted by the patient and his physician.

Example 7

A male patient was diagnosed with Peyronie's disease by his physician. He began treatment with streptolysin O at a rate and amount of one (2 units/0.05 ml) drop, three times daily by sublingual administration. After 30 days of treatment, improvements in the contracture of his penis were noted by the patient and his physician.

Example 8

Bovines, which have lost one or more quarters to mastitis, were treated using one dose of streptolysin O (2 units/0.05 ml) drop, twice daily for thirty days by subcutaneous administration. The quarters damaged due to mastitis were reclaimed and produced milk after treatment.

Example 9

According to this example, streptolysin O was administered to a 27 year old human female with a history of failure to conceive. The subject was diagnosed as suffering with fibroid scarring on the uterus and fallopian tubes and was assessed as having less than a 20% chance of becoming pregnant. Specifically, streptolysin O was administered at the rate of one (2 units/0.05 ml) drop, four times daily by sublingual administration. The subject became pregnant within six weeks of the initiation of therapy and successfully delivered a healthy child.

Example 10

According to this example, streptolysin O was administered to ten mares diagnosed as suffering from periglandular or uterine fibrosis. Mares can become infertile after several pregnancies as a consequence of periglandular or uterine fibrosis which prevents implantation and/or dilation of the uterus such as to be insufficient to accommodate the growing fetus.

Ten mares diagnosed as suffering from periglandular or uterine fibrosis were treated by subcutaneous administration of streptolysin O at a dosage of 2 units per dose (0.2 cc). The horses were treated by streptolysin O administration twice daily for two weeks followed by one dose daily for one week. The results of histopathological evaluation of the first three horses by endometrial biopsies both before and after treatment are set out in Table I below. Such endometrial biopsies are graded as category I (essentially normal) through categories IIA, IIB, and III with category III being the worst.

TABLE I

| Horse No. | Initial Evaluation | Evaluation 60 Days Post Treatment |
| --- | --- | --- |
| 1 | IIB-III | IIB |
| 2 | III | IIB |
| 3 | III | IIA |

The first three horses were bred after administration of the streptolysin O and two of the horses were safely in foal (having been carrying a live fetus more than 50 days). The fourth horse was not bred but was also found to have reduced uterine fibrosis as determined by endometrial biopsy. Of the next six horses no histopathological evaluation was available but three had conceived after treatment according to the invention.

Example 11

According to this example, the neuroprotective effects of streptolysin O were determined in a glutamate intoxication model utilizing the nerve nerve-muscle co-culture developed by Askanas and Engel, Neurology 25:58-67 (1975). This culture makes it possible to create striated human muscle fiber innervations with rat spinal chord explants and dorsal root ganglions. After 15 days of co-culture, the muscle fibers show spontaneous contractile activity. In this co-culture, it is then possible to induce cell death by intoxication using neurotoxic agents such as glutamate or hydrogen peroxide. Such intoxications are time dependent and the viability and functionality of the motoneurons can be studied from two parameters: muscle contractile activity and apoptosis induction, quantified by an ELISA method on the basis of quantification of cytoplasmic histone-associated DNA fragments.

Glutamate is the main excitatory neurotransmitter in the mammalian CNS, but over-stimulation of its receptors causes neuro-degeneration. According to empirical protocol, in nerve-muscle co-cultures, 10 mM of glutamate in the medium decreases contractile activity after one day and cause motoneuron cell death by apoptosis after 1 week. This motoneuron cell death induces muscle fiber degeneration.

According to this example, streptolysin O at two concentrations, 0.01% and 1% (four wells per condition) was incubated for 9 days in an established nerve-muscle co-culture. The conditioned culture media was replaced each day. Cultures were then intoxicated with either glutamate 10 mM or hydrogen peroxide ($H_2O_2$) 800 µM and the neurotoxic effects were evaluated by (1) quantification of the frequency of contractions and (2) by cell death level as measured by quantification of apoptosis.

The contraction frequency of the cells was then measured and recorded by image analysis software respectively before incubation, after 1 hour, 24 hours, 48 hours and 72 hours of intoxication with or without incubation with streptolysin O 0.01% and 1% on their own. The results are given as a percentage of the contraction frequency compared to the contraction frequency before incubation expressed as 100%. Two co-incubations were tested, glutamate 10 mM and $H_2O_2$ 800(M with the product SO 0.01% and 1% (4 wells per condition). These results show that streptolysin O was responsible for a dramatic increase of the contraction frequency reaching a plateau after 24 hours, 48 hours and 72 hours.

After 24 hours incubation with a 10 mM concentration of glutamate an increase in the contraction frequency of the selected muscle fibers was observed. After 48 hours incubation with a 10 mM glutamate concentration the contraction frequency of the muscle fiber decreased to reach a lower level than its basic level. The contraction frequency after 10 mM glutamate intoxication in combination with streptolysin O incubation increased during the first 24 hours and after 48 hours remained higher than glutamate intoxication on its own.

The effect of streptolysin O on the contraction frequency of a muscle fiber (4 wells per condition) selected from a nerve-muscle co-culture after 1 hour, 24 hours, 48 hours and 72 hours of intoxication with 10 mM L-glutamate. Specifically, the data are shown at two concentrations (0.01% and 1%) compared to a normalized control response before incubation expressed as 100%.

The results shown in FIG. 1 illustrates that the contraction frequency, with streptolysin O at 0.01%, dramatically increased to reach a plateau of almost 250% of the control response and that at a streptolysin O concentration of 1% increase the contraction frequency even greater.

Figure 2:
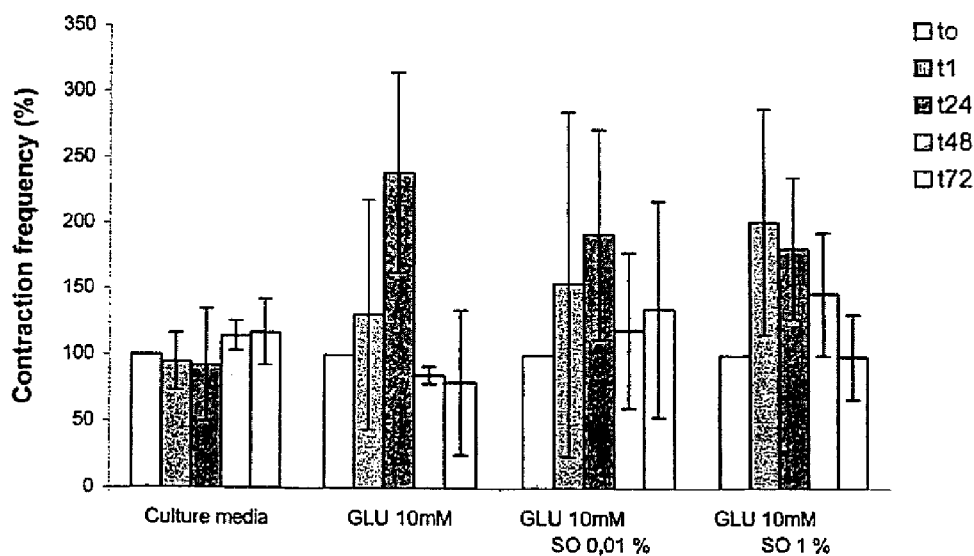
FIG. 2 depicts the effects of streptolysin O on the contraction frequency in a nerve muscle co-culture in a glutamate intoxication model.

The effect of SO at two concentrations (0.01% and 1%) on the contraction frequency of nerve muscle co-cultures intoxicated with 10 mM L-glutamate compared to the normalized control response before incubation expressed as 100% (4 fibers analysed per condition) is shown in FIG. 2. FIG. 2 illustrates that the contraction frequency after 1 hour and 24 hours of incubation with 10 mM L-glutamate dramatically increased and shows wide standard deviations. After 48 hours incubation, the contraction frequency of the muscle fiber decreased to recover its basic level (100%).

After a 1-hour incubation period, the effect of streptolysin O at 0.01% after 10 mM L-Glutamate intoxication showed an increase to almost 150% of the control response and was almost to 200% after 24 hours. After 48 and 72 hours, the contraction frequency still reached more than 120% of the control response. After a 1-hour incubation period in presence of 10 mM glutamate, SO 149 1% lead to an increase to almost 200% of the control response and was almost the same after 24 hours. After 48 hours, the contraction frequency still reached 150% and it recovered the basic level (100% of the control response) after 72 hours.

These results show that after 10 mM Glutamate intoxication, streptolysin O has both a myostimulating effect and a neuroprotective effect analyzed by a cell apoptosis quantification.

Example 12

According to this example, the neuroprotective effects of streptolysin O were analyzed by quantification of cell apoptosis after 9 days of hydrogen peroxide intoxication (800 µM) and Glutamate (10 mM L-glutamate) intoxication. Negative and positive apoptosis controls were respectively (a) culture media, (b) glutamate 10 mM and (c) $H_2O_2$ 800 µM and apoptosis was evaluated using a Cell Death Detection ELISA kit" (Roche).

Specifically, the occurrence of apoptosis of nerve muscle co-cultures was measured using Optic Density at 405 nm after 9 days of (a) incubation with streptolysin O at two concentrations, 0.01% and 1% (b) intoxication with 10 mM L-glutamate and 800 µM hydrogen peroxide and (c) incubation with both L-glutamate 10 mM and hydrogen peroxide 800 µM in combination with streptolysin O at two concentrations 0.01% and 1%.

The results showed that the level of cell death from apoptosis within the culture with streptolysin O 0.01% was approximately the same as the control culture (0.3 OD). The glutamate intoxications showed a cell death level from apoptosis which was approximately the same as the control culture. The cell death level from apoptosis within the culture with both the glutamate and SO 0.01% or 1% incubation was similar to the control culture. The hydrogen peroxide intoxication showed that cell death level is slightly higher than the control culture. The cell death level with both the hydrogen peroxide and streptolysin O at concentrations of 0.01% or 1% incubation was similar to the culture intoxicated with hydrogen peroxide. These results suggest that the neuroprotective effects of streptolysin O are not related to an anti-apoptotic effect.

Example 13

According to this Example, a competitive inhibition assay was carried out between the hyaluronic acid and streptolysin O on human keratinocyte CD44 receptors. Streptolysin O incubated in the medium of five different keratinocyte and melanocyte human primary cultures did not induce cytotoxicity. However in the same culture conditions, streptolysin O at both 1× and 0.1× concentrations induced an increase of keratinocyte cell growth but not melanocyte cell growth.

The evaluation of incidence of streptolysin O on cell surface markers of keratinocytes using microscopy analysis was determined by an immunofluorescence labeling carried out with monoclonal antibodies. Streptolysin O was found to have an influence on five keratinocyte markers (CD44, CD47, CD40, CD49-c and MMP-2). In particular, streptolysin O at 1×, 0.1× and 0.01× appeared to maintain expression of CD44 in keratinocytes after 26 hours of culture compared to loss of staining with placebo.

It has also been observed that CD44 was the hyaluronic acid receptor (HA). In order to determine the effects of streptolysin O in the CD44-HA function, a competitive inhibition assay was carried out between hyaluronic acid (HA) and streptolysin O on the keratinocyte CD44 receptor. Specifically, a competitive inhibition between hyaluronic acid (HA) and streptolysin O (MIL001) on the keratinocyte CD44 receptor was tested on 01-010 cell culture (15 000 keratinocytes/well). This culture were treated with at (1) streptolysin O concentration (0.01×) and at six (6) different hyaluronic acid HA concentrations (0%, 0.0001%, 0.0005%, 0.001%, 0.005% and 0.01%) and at 3 different incubation times (1, 20, and 44 hours). The inhibition was measured by an immunofluorescence labeling performed with the anti Human CD44 monoclonal antibody using microscopic analysis.

Specifically, normal human keratinocytes were thawed and seeded with KGM medium (BioWhittaker, Md.) during the first passage. At subconfluence, keratinocytes were trypsinized, enumerated and cultured with KGM medium in flat-bottomed microtiter plates with 15 000 keratinocytes per well. The cultures were incubated at 37° C. in a humidified 5% $CO_2$ atmosphere.

Streptolysin O 100× (200 units) was diluted at 0.01×. was added or not (control placebo) in 96 well microplates 24 hours after the cell seeding and maintained in culture for 1 hour, 20 hours and 44 hours. Different concentrations of hyaluronic acid solution at 0.1%, 0.05%, 0.01%, 0.005% and 0.001% were diluted at 1/10 in the different culture wells and added to the wells. At the end of each incubation time (1 hour, 20 hours and 44 hours), the keratinocytes were washed and fixed 5 minutes with ethanol/acetic acid (95/5) at −20° C. Cells were then extensively washed with buffer solution and were stored at 4° C. until staining with monoclonal antibodies to human CD44 antigen phycoerythrin labeled (Caltag Laboratories).

A quantitative results analysis was then carried out on each culture. This quantitative analysis gives the tendency of the CD44 immunostaining with placebo or MIL001 0.01× as a function of HA concentration. The results show that for placebo samples CD44 staining is increased at the 2 higher HA concentrations 0.001% and 0.01%; however at 0.005% the staining is similar to lower HA concentrations.

The results after 1 hour and after 20 hours of culture showed no statistically significant difference between streptolysin O and placebo with respect to inhibiting hyaluronic acid binding to the CD44 receptor.

The results after 44 hours of culture show that CD44 expression is stronger with MIL001 0.001× in the presence of 0% hyaluronic acid than with placebo and confirms that streptolysin O increases CD44 expression on keratinocytes. CD44 staining is stronger with the mixture of MIL001 0.001× with 0.0001% hyaluronic acid but decreases with other concentrations of hyaluronic acid back to levels observed with placebo. Thus, hyaluronic acid inhibits the effect of streptolysin O at MIL001 0.001× which has been demonstrated to increase CD44 receptor expression compared to placebo.

The results after 44 hours of competition also indicate that lower concentrations of hyaluronic acid (0.0001% and 0.0005%) increase CD 44 receptor expression compared to the absence of hyaluronic acid. Then the expression of CD 44 decreases at higher HA concentrations yet is still higher than with the negative control (placebo+HA 0%).

Further, in samples incubated with streptolysin O at MIL001 0.001× CD44 receptor expression is constant compared to results obtained in the absence of hyaluronic acid whatever hyaluronic acid concentration is present in the culture. In other words, hyaluronic acid has no effect on CD44 receptor expression on keratinocytes in culture in the presence of streptolysin O at MIL001 0.001×.

Moreover, the results show that HA inhibits the increased expression of CD44 receptor on keratinocytes induced by MIL001 0.01× incubation and thereby shows competition between streptolysin O (MIL001) and hyaluronic acid (HA) for CD44 receptor binding after 44 hours of culture.

Example 14

A 3-year old thoroughbred gelding suffered an acute tear of the medial branch of the right front suspensory ligament. After being treated for 30 days with streptolysin-O (0.2 cc streptolysin O twice daily (2 Units per dose) by subcutaneous administration) the attending veterinarian reported "significant resolution" of the medial branch.

Example 15

A 3-year old thoroughbred colt had a small tear in the superficial digital flexor tendon. After being treated for 30 days with streptolysin-O (0.2 cc streptolysin O twice daily (2 Units per dose) by subcutaneous administration), the tear had significantly improved and the horse was being hand-walked daily.

Example 16

A 2-year old Standardbred filly, a trotter used competitively, presented with a lame right front leg graded by the attending veterinarian as being a three out of a possible five with respect to severity. There was moderate effusion and pain associated with the lateral suspensory branch. A core lesion on the suspensory branch was detected by ultrasound. The filly was treated with streptolysin-O (0.2 cc streptolysin O twice daily (2 Units per dose) by subcutaneous administration for thirty days and then once daily thereafter) combined with stall rest for sixty days. At sixty days, there was no pain or effusion, the lesion size was significantly reduced, and the filly was sound when trotting, thus able to return to normal training.

Numerous modifications and variations in the practice of the invention are expected to occur to those of skill in the art upon consideration of the presently preferred embodiments thereof. Consequently, the only limitations which should be placed upon the scope of the invention are those which appear in the appended claims.

What is claimed is:

1. A method of alleviating the symptoms associated with a connective tissue disorder, wherein the disorder is tendonitis, comprising administering to a subject in need thereof streptolysin O in an amount effective to treat one or more symptoms of said connective tissue disorder.

2. The method of claim 1, wherein the tendonitis is equine tendonitis.

3. The method of claim 1, where said streptolysin O is administered by a mode selected from the group consisting of sublingual, bucal, oral drench, subcutaneous, intradermal, intravenous, intramuscular, intrathecal, inhalation, and topical.

4. The method of claim 3, wherein said streptolysin O is administered sublingually.

5. The method of claim 1, wherein said streptolysin O is administered at a dosage from about 0.0032 units to about 50 units.

6. The method of claim 1, wherein said streptolysin O is administered at a dosage from about 0.05 units to about 10 units.

7. The method of claim 1, wherein said streptolysin O is administered at a dosage from about 0.01 units to about 1.0 unit.

* * * * *